United States Patent
Pollock et al.

(10) Patent No.: US 6,450,811 B1
(45) Date of Patent: Sep. 17, 2002

(54) DENTAL SCALER SYSTEM AND METHOD

(75) Inventors: David P. Pollock, York, PA (US); Kent D. Russell, Seven Valleys, PA (US); Kevin K. Lint, York, PA (US); Bryan M. Woolsey, Thurmont, MD (US)

(73) Assignee: Dentsply Research & Development Corp.

(*) Notice: Subject to any disclaimer, the term of this patent is extended or adjusted under 35 U.S.C. 154(b) by 0 days.

(21) Appl. No.: 09/467,494

(22) Filed: Dec. 20, 1999

Related U.S. Application Data
(60) Provisional application No. 60/156,000, filed on Sep. 24, 1999.

(51) Int. Cl.⁷ .............................................. A61C 17/02
(52) U.S. Cl. ............................................ 433/86; 433/80
(58) Field of Search ............................ 433/80–88, 119

(56) References Cited

U.S. PATENT DOCUMENTS

| | | | |
|---|---|---|---|
| 3,213,537 A | * 10/1965 | Balamuth et al. | |
| 3,809,977 A | 5/1974 | Balamuth et al. | 318/116 |
| 3,924,335 A | 12/1975 | Balamuth et al. | |
| 3,931,533 A | 1/1976 | Raso et al. | 310/8.1 |
| RE28,752 E | 3/1976 | Balamuth et al. | 318/116 |
| 4,069,587 A | 1/1978 | Peralta | |
| 4,148,309 A | 4/1979 | Reibel | 128/24 |
| 4,171,572 A | 10/1979 | Nash | |
| 4,193,197 A | 3/1980 | Kuris et al. | 433/82 |
| 4,271,371 A | 6/1981 | Furuichi et al. | 310/316 |
| 4,286,949 A | * 9/1981 | Holt, Jr. | 433/103 |
| 4,371,816 A | 2/1983 | Wieser | 318/116 |
| 4,403,176 A | 9/1983 | Cranston | 318/114 |
| 4,492,574 A | 1/1985 | Warrin et al. | 433/81 |
| 4,669,453 A | 6/1987 | Atkinson et al. | 128/66 |
| 4,830,210 A | 5/1989 | Mabille | 215/309 |
| 4,906,187 A | * 3/1990 | Amadera | 433/80 |
| 5,120,219 A | * 6/1992 | De Farcy | 433/88 |
| 5,125,837 A | 6/1992 | Warrin et al. | 433/98 |
| 5,211,558 A | * 5/1993 | Bailey et al. | 433/77 |
| 5,344,317 A | 9/1994 | Pacher et al. | 433/85 |
| 5,419,703 A | 5/1995 | Warrin et al. | 433/216 |
| 5,451,161 A | 9/1995 | Sharp | 433/119 |
| 5,697,784 A | 12/1997 | Hafele et al. | 433/85 |
| 5,730,594 A | 3/1998 | Sharp | 433/119 |
| 5,754,016 A | 5/1998 | Jovanovic et al. | 318/118 |
| 5,820,373 A | * 10/1998 | Okano et al. | 433/80 |
| 5,853,290 A | * 12/1998 | Winston | 433/86 |
| 5,927,977 A | 7/1999 | Sale et al. | 433/86 |
| 6,030,212 A | * 2/2000 | Schuman et al. | 433/80 |
| 6,106,288 A | * 8/2000 | Brassil et al. | 433/88 |
| 6,293,793 B1 | * 9/2001 | Schuman et al. | 433/86 |

FOREIGN PATENT DOCUMENTS

WO   98/23222   6/1998

* cited by examiner

Primary Examiner—Ralph A. Lewis
(74) Attorney, Agent, or Firm—Dale R. Lovercheck; James B. Bieber

(57) ABSTRACT

The method of dental scaling of the invention uses a scaler and reservoir system, comprising: a scaler handpiece having a scaling tip, a scaler housing enclosing a scaler valve, a compressor housing enclosing a reservoir valve and a compressor, a reservoir housing having an inner chamber, the scaler housing is supported by the reservoir housing, and the compressor housing is supported by and connected to the scaler housing and the reservoir housing, the scaler handpiece is connected to the scaler housing, vibrates the tip, and scales a tooth in a patient'smouth by positioning the scaling tip adjacent to the tooth. Preferably the dental scaler and reservoir system, comprising: a scaler housing, a scaler valve, a compressor housing, a reservoir valve, a compressor, a reservoir housing having an inner chamber, a handpiece housing having a handpiece valve and a vibrational member. The scaler housing is supported by the reservoir housing. The compressor is connected to compressor conduit. The compressor conduit is connected to the inner chamber of the reservoir housing thereby providing fluid flow communication between the compressor and the inner chamber of the reservoir housing. The inner chamber of the reservoir housing is connected to reservoir conduit. The reservoir conduit is connected to the reservoir valve thereby providing in fluid flow communication between the inner chamber and the reservoir valve. The reservoir valve is connected to handpiece conduit The handpiece conduit is connected to the handpiece valve thereby providing fluid flow communication between the reservoir valve and the handpiece valve.

24 Claims, 16 Drawing Sheets

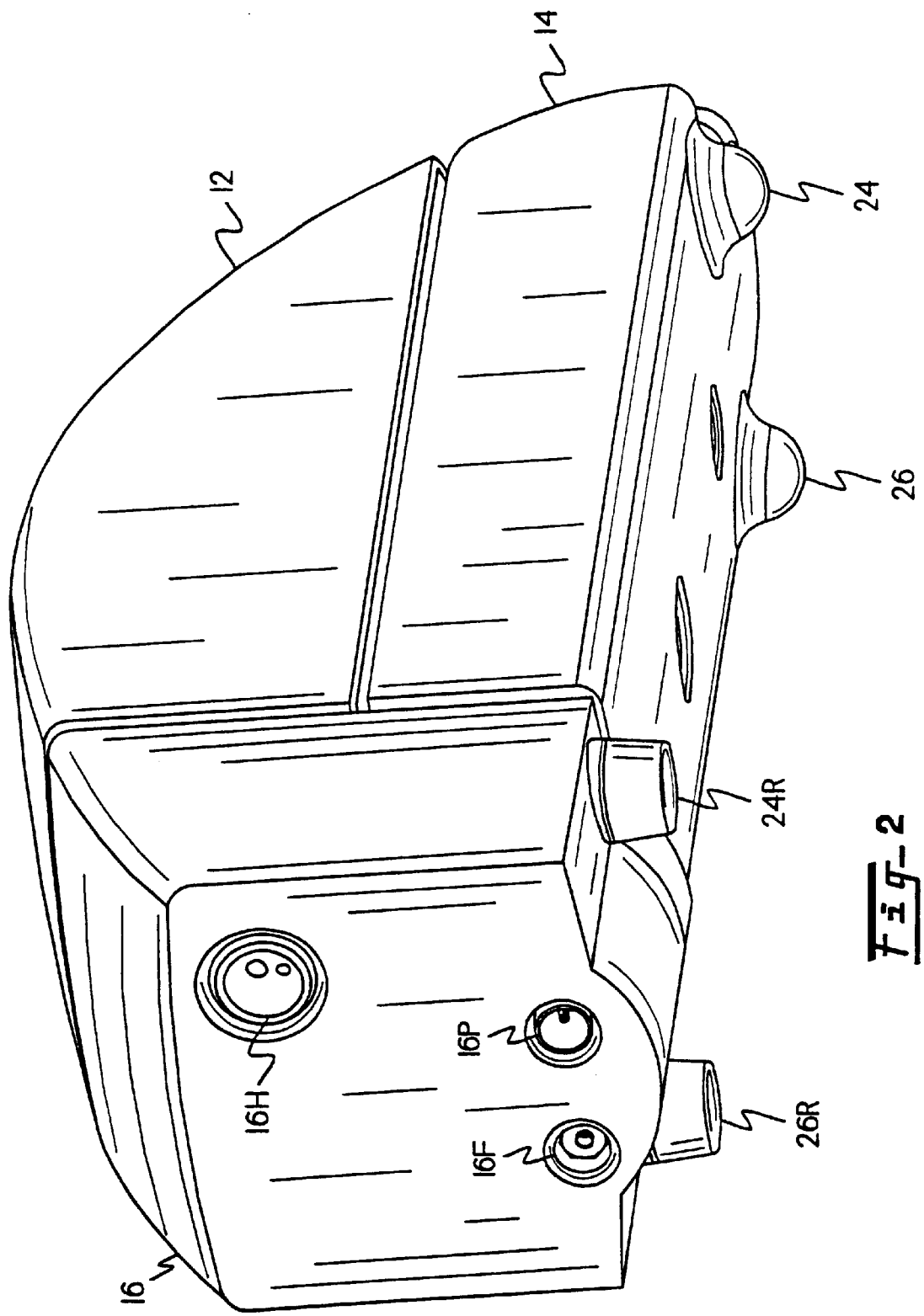

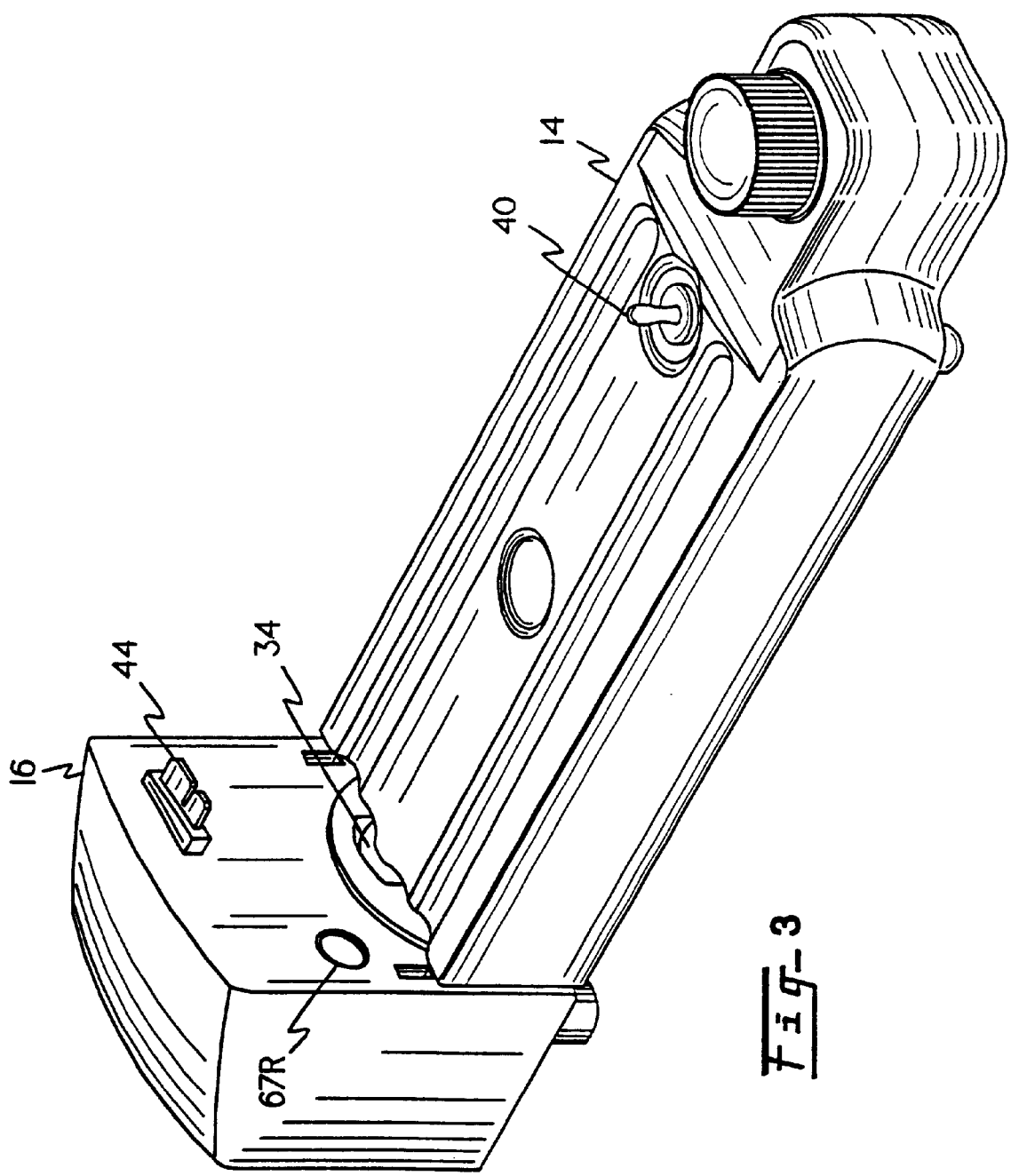

Fig_7

Fig_8

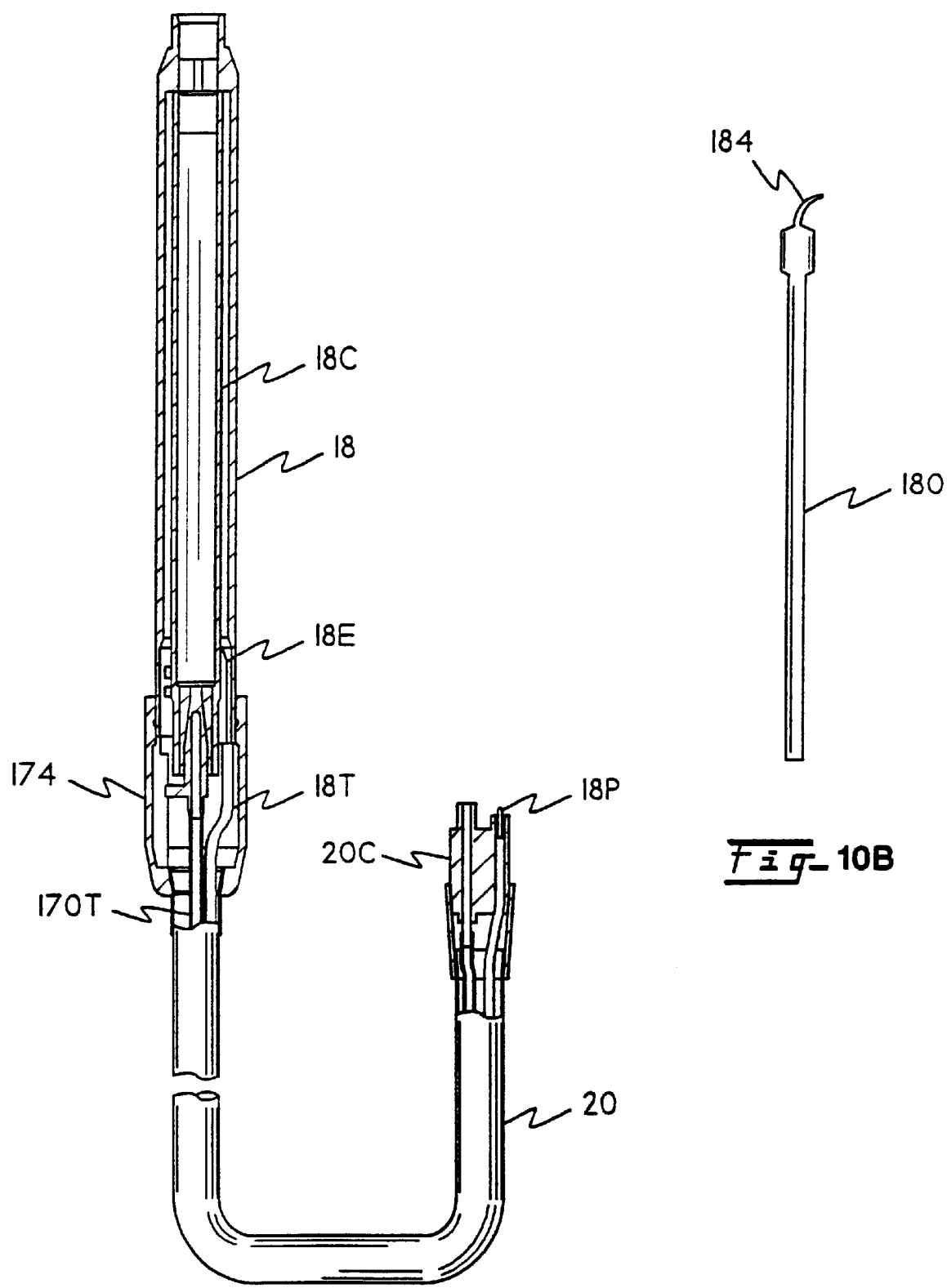

Fig_15 ns and methods of scaling teeth. More specifically the invention provides an improved dental scaler and method of scaling teeth.

DENTAL SCALER SYSTEM AND METHOD

This application claims the benefit of provisional patent application Ser. No. 60/156,000 filed Sep. 24, 1999 incorporated herein by reference in its entirety.

The invention relates to dental scalers and methods of scaling teeth. More specifically the invention provides an improved dental scaler and method of scaling teeth.

BACKGROUND OF THE INVENTION

Schuman et al disclose a dental scaler and reservoir system in U.S. Pat. No. 6,030,212. Prior art dental scaler and reservoir systems do not support a dental scaler on a reservoir and connect it to a compressor system, as is provided by the present invention. Prior art dental scaler and reservoir systems do not provide a dental scaler, which is operable both with and without a reservoir, as is provided by the present invention. The prior art does not provide a dental scaler and reservoir system, having a scaler housing enclosing a scaler valve, a compressor housing enclosing a reservoir valve and a compressor, a reservoir housing having an inner chamber, wherein the scaler housing is supported by the reservoir housing, and the compressor housing is supported by and connected to the scaler housing and the reservoir housing. The prior art does not provide a method of using a dental scaler system, comprising: providing a first scaler conduit and a dental scaler system comprising a scaler system comprising a scaler housing enclosing a second scaler conduit, and scaler valve, the first scaler conduit not being connected in fluid flow communication with the scaler valve, providing a handpiece system comprising scaler tip and a handpiece housing enclosing a handpiece conduit and handpiece valve, connecting the handpiece conduit in fluid flow communication to the first scaler conduit, conveying a first fluid through the first scaler conduit, scaler valve, and handpiece valve to the scaler tip, connecting the handpiece conduit in fluid flow communication to the second scaler conduit, and conveying a second fluid through the second scaler conduit, and handpiece valve to the scaler tip. Nor does the prior art provide a method of using a dental scaler system, comprising providing a dental scaler system comprising a scaler system, a compressor system and a handpiece system. The scaler system comprising a scaler housing enclosing a scaler conduit, and scaler valve. The compressor system comprises a reservoir and a compressor housing enclosing a compressor and a compressor conduit. The reservoir comprising a container enclosing reservoir fluid in a container chamber. The handpiece system comprising scaler tip and a handpiece housing enclosing a handpiece conduit and handpiece valve. The handpiece conduit is connected in fluid flow communication to compressor conduit. At least a portion of the reservoir fluid is conveyed through the compressor conduit, scaler valve, and handpiece valve to the scaler tip. The handpiece conduit is connected in fluid flow communication to the scaler conduit and water conveyed through the scaler conduit, and handpiece valve to the scaler tip. When the handpiece conduit is connected in fluid flow communication to the compressor conduit, the compressor housing is connected to the scaler housing and the reservoir housing, the scaler handpiece is supported by the reservoir housing. When the handpiece conduit is connected in fluid flow communication to the scaler conduit, the scaler housing is supported by a substantially horizontal surface.

The problems of the prior art are overcome by the present invention.

OBJECTS OF THE INVENTION

It is an object of the invention to provide a dental scaler and reservoir system supporting a dental scaler on a reservoir and connect it to a compressor system.

It is an object of the invention to provide a dental scaler and reservoir systems providing a dental scaler which is operable both with and without a reservoir.

It is an object of the invention to provide a dental scaler and reservoir system, having a scaler housing enclosing a scaler valve, a compressor housing enclosing a reservoir valve and a compressor, a reservoir housing having an inner chamber, wherein the scaler housing is supported by the reservoir housing, and the compressor housing is supported by and connected to the scaler housing and the reservoir housing.

It is an object of the invention to provide a method of dental scaling of the invention uses a scaler and reservoir system, comprising: a scaler handpiece having a scaling tip, a scaler housing enclosing a scaler valve, a compressor housing enclosing a reservoir valve and a compressor, a reservoir housing having an inner chamber, the scaler housing is supported by the reservoir housing, and the compressor housing is supported by and connected to the scaler housing and the reservoir housing, the scaler handpiece is connected to the scaler housing, vibrates the tip, and scales a tooth in a patient's tooth by positioning the scaling tip adjacent to the tooth.

It is an object of the invention to provide a method of using a dental scaler system, comprising: providing a first scaler conduit and a dental scaler system comprising a scaler system comprising a scaler housing enclosing a second scaler conduit, and scaler valve, the first scaler conduit not being connected in fluid flow communication with the scaler valve, providing a handpiece system comprising scaler tip and a handpiece housing enclosing a handpiece conduit and handpiece valve, connecting the handpiece conduit in fluid flow communication to the first scaler conduit, conveying a first fluid through the first scaler conduit, scaler valve, and handpiece valve to the scaler tip, connecting the handpiece conduit in fluid flow communication to the second scaler conduit, and conveying a second fluid through the second scaler conduit, and handpiece valve to the scaler tip.

It is an object of the invention to provide a method of using a dental scaler system, comprising providing a dental scaler system comprising a scaler system, a compressor system and a handpiece system. The scaler system comprising a scaler housing enclosing a scaler conduit, and scaler valve. The compressor system comprises a reservoir and a compressor housing enclosing a compressor and a compressor conduit The reservoir comprising a container enclosing reservoir fluid in a container chamber. The handpiece system comprising scaler tip and a handpiece housing enclosing a handpiece conduit and handpiece valve. The handpiece conduit is connected in fluid flow communication to compressor conduit. At least a portion of the reservoir fluid is conveyed through the compressor conduit, scaler valve, and handpiece valve to the scaler tip. The handpiece conduit is connected in fluid flow communication to the scaler conduit and water conveyed through the scaler conduit, and handpiece valve to the scaler tip.

BRIEF DESCRIPTION OF THE DRAWING

FIG. 2 is a rear perspective view of a dental scaler and reservoir system in accordance with the invention.

FIG. 3 is a frontal perspective view of the compressor housing and reservoir housing of the dental scaler and reservoir system in accordance with the invention shown in FIGS. 1 and 2.

FIG. 10A is a cross-sectional side view of a handpiece, conduit and connector for use with the dental scaler and reservoir system in accordance with the invention shown in FIGS. 1 and 2.

FIG. 10B is a side view of an insert for a handpiece for use with the dental scaler and reservoir system in accordance with the invention shown in FIGS. 1 and 2.

SUMMARY OF THE INVENTION

Figure 1:
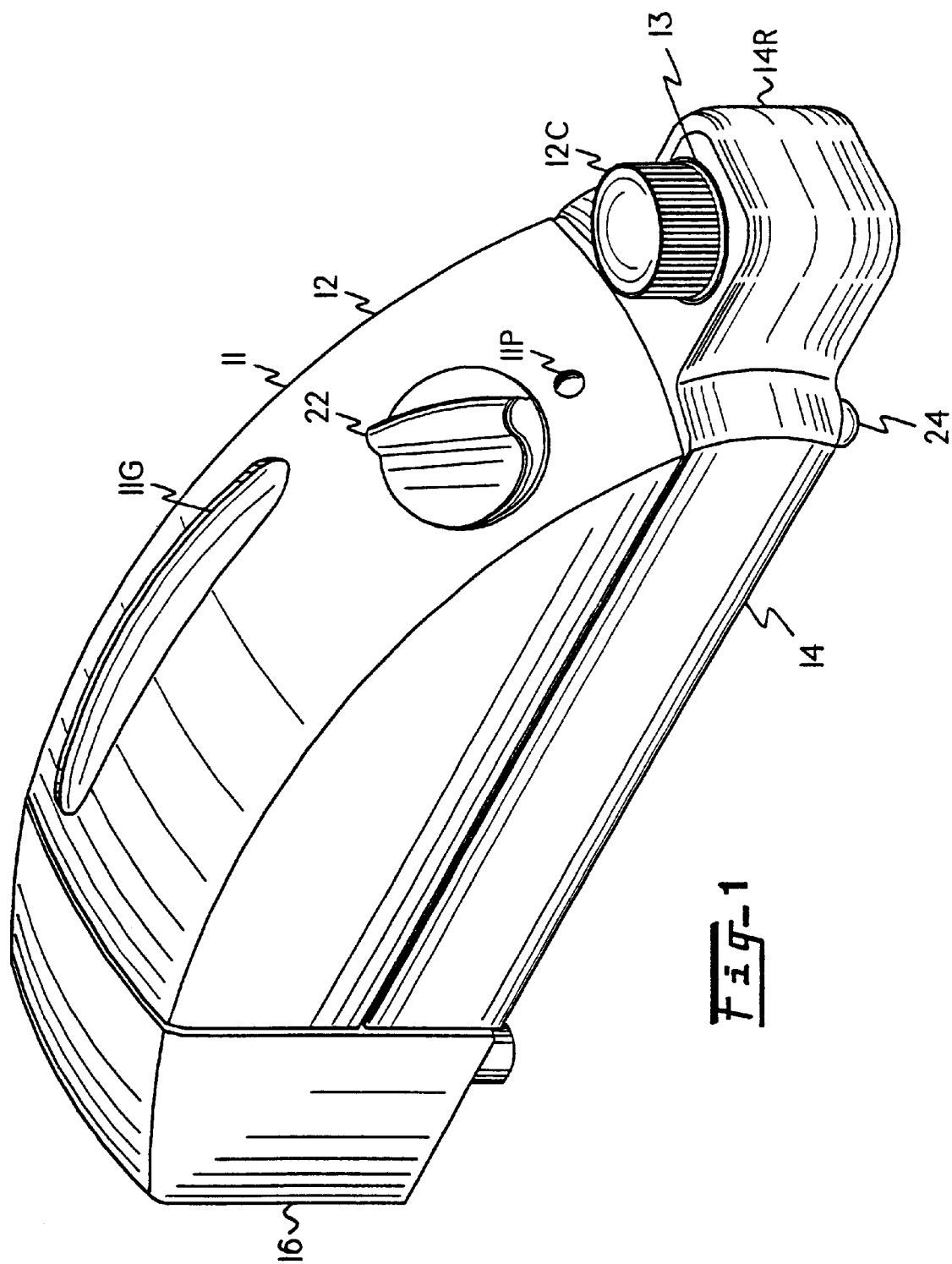
FIG. 1 is a frontal perspective view of a dental scaler and reservoir system in accordance with the invention.
Figure 3A:
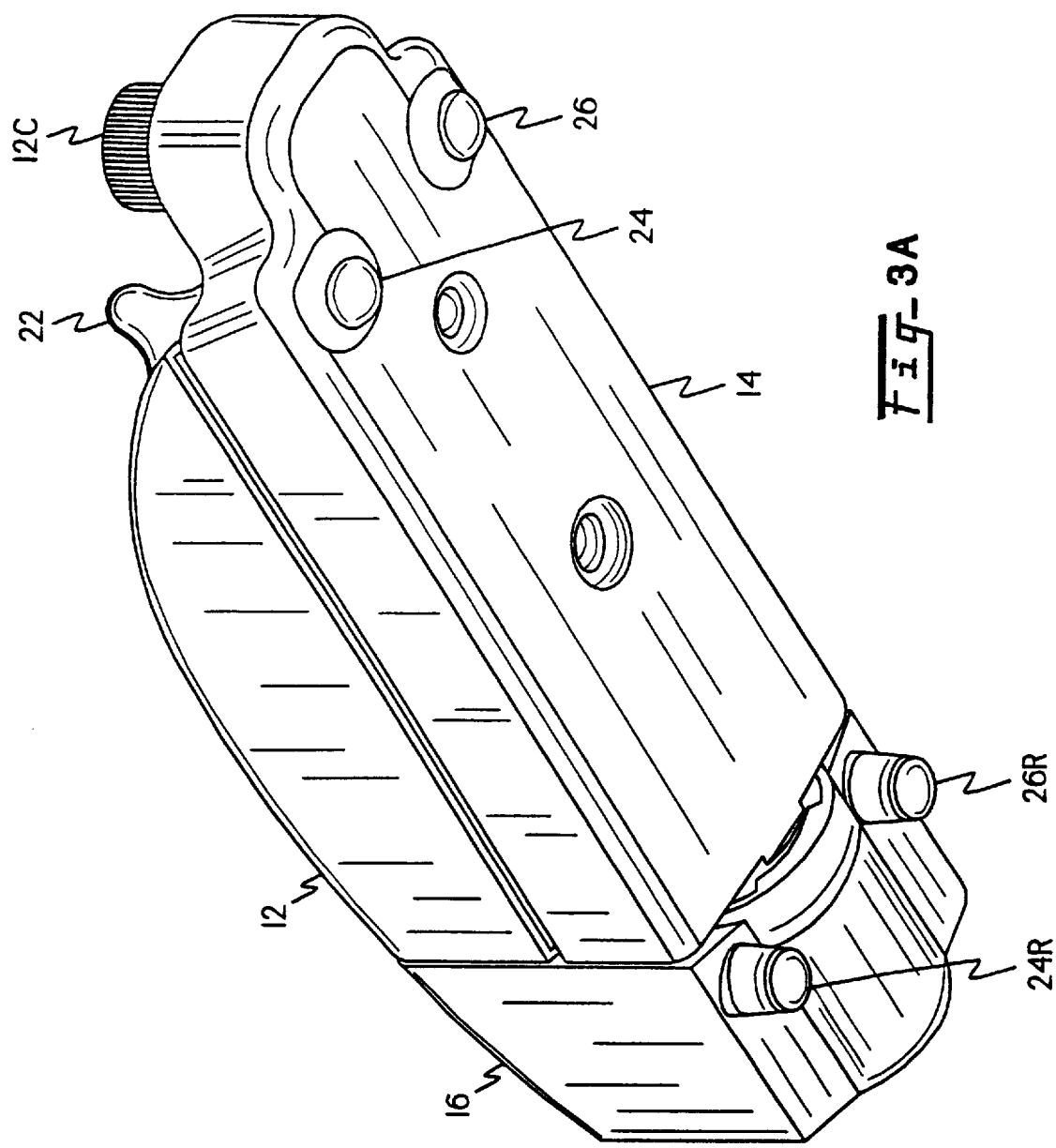
FIG. 3A is a bottom perspective view of a dental scaler and reservoir system in accordance with the invention.
Figure 4:
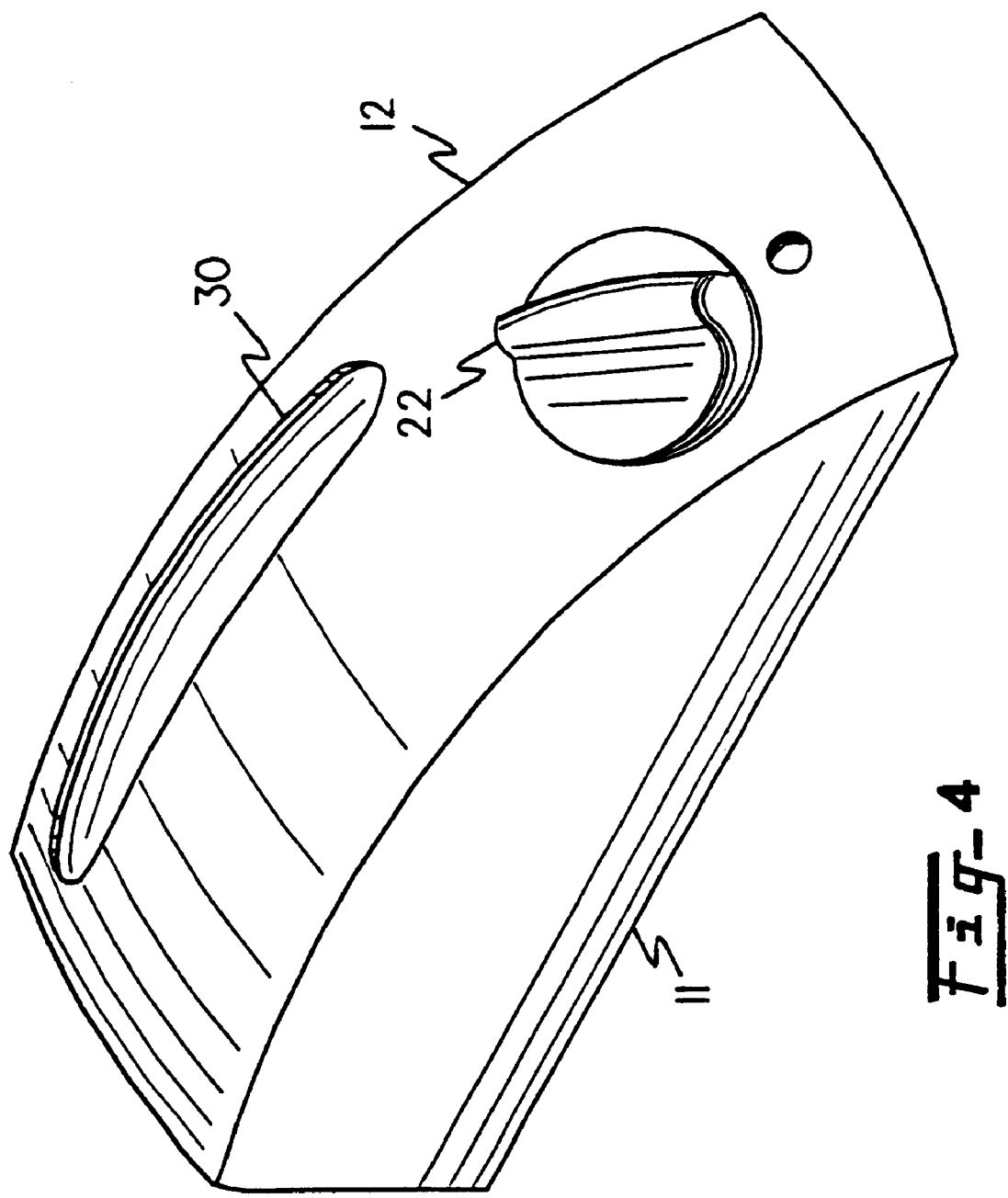
FIG. 4 is a frontal perspective view of the dental scaler of the dental scaler and reservoir system in accordance with the invention shown in FIGS. 1 and 2.
Figure 5:
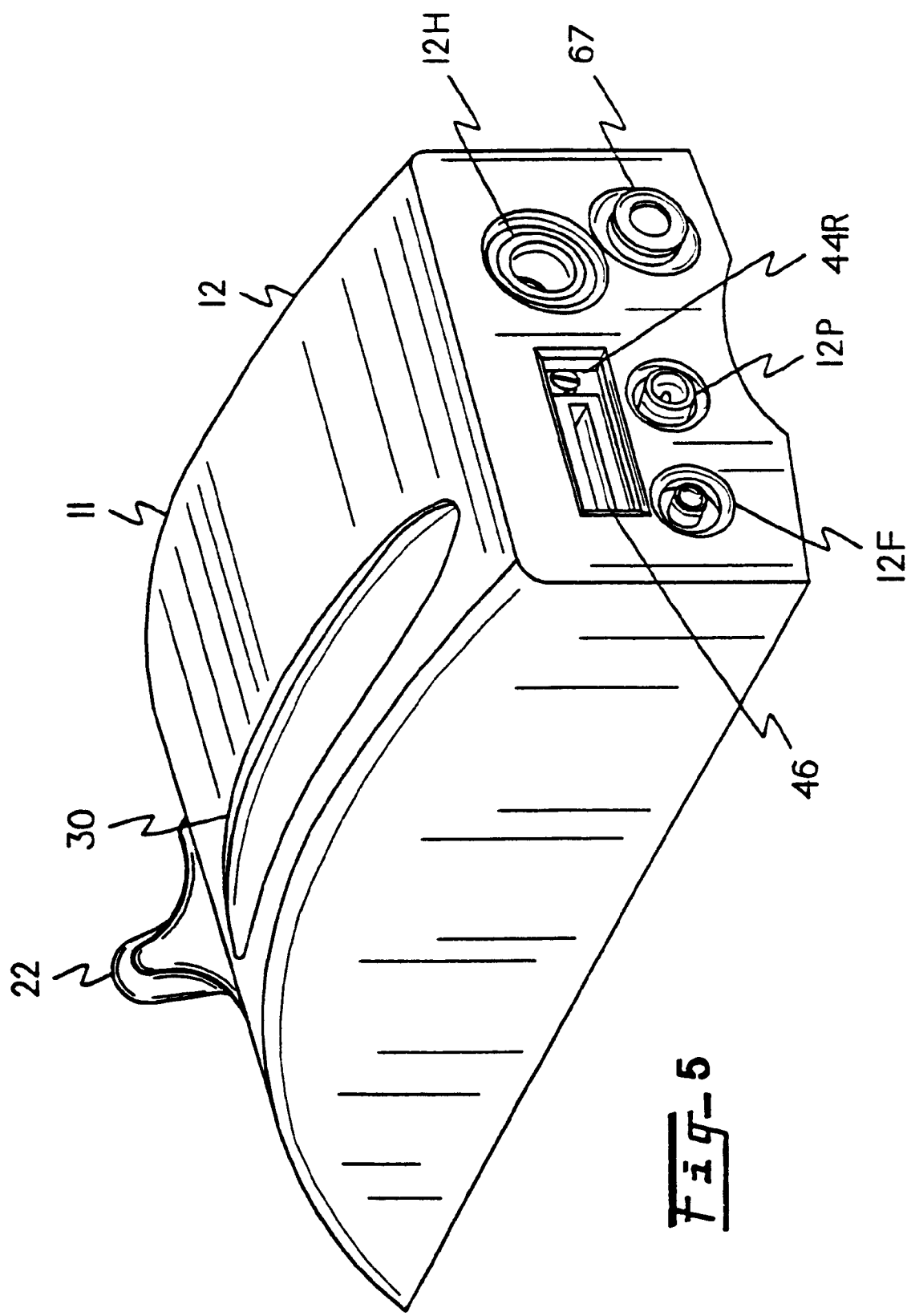
FIG. 5 is a rear perspective view of the dental scaler the dental scaler and reservoir system in accordance with the invention shown in FIGS. 1 and 2.
Figure 6:
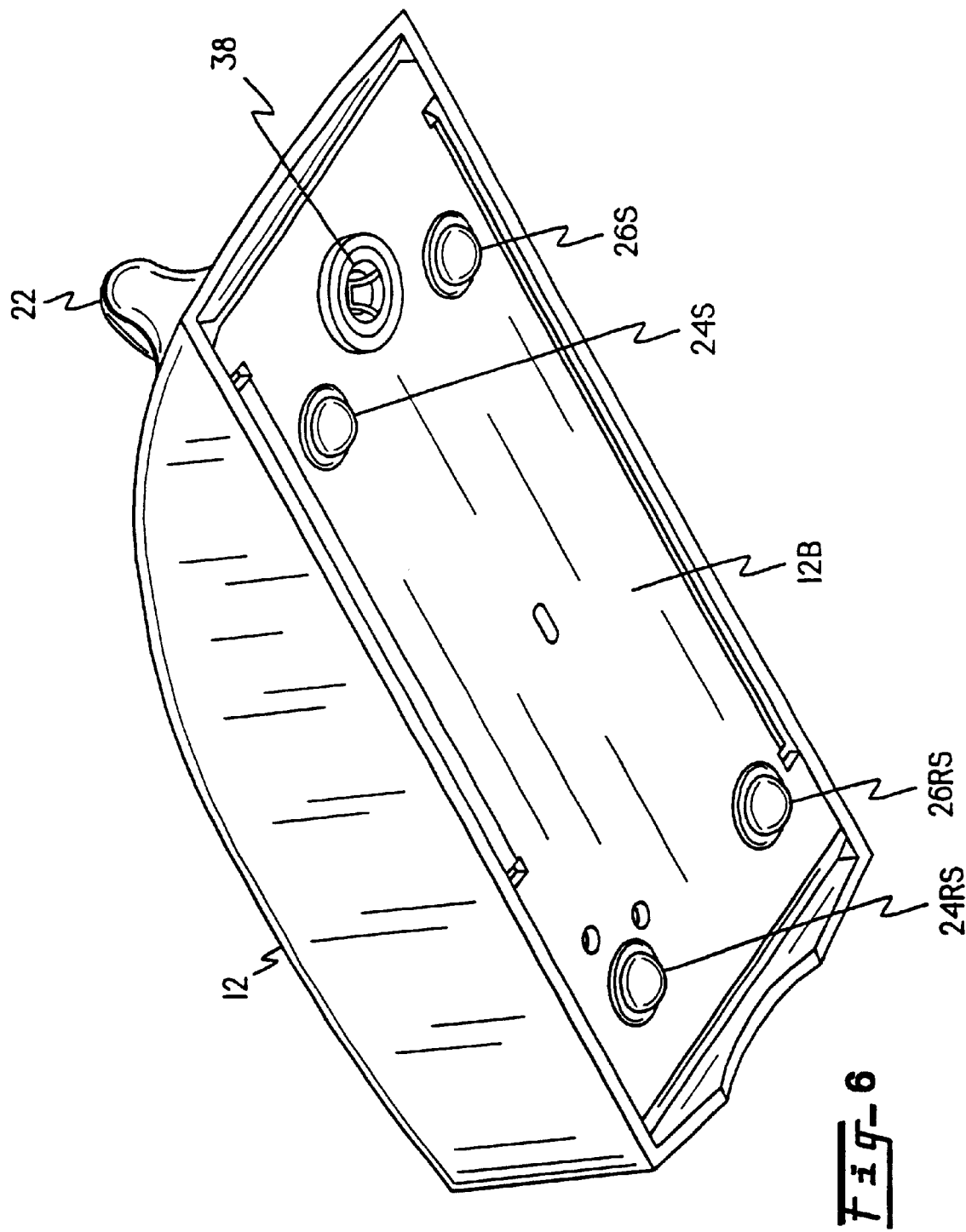
FIG. 6 is a bottom perspective view of the dental scaler of the dental scaler and reservoir system in accordance with the invention shown in FIGS. 1 and 2.
Figure 7:
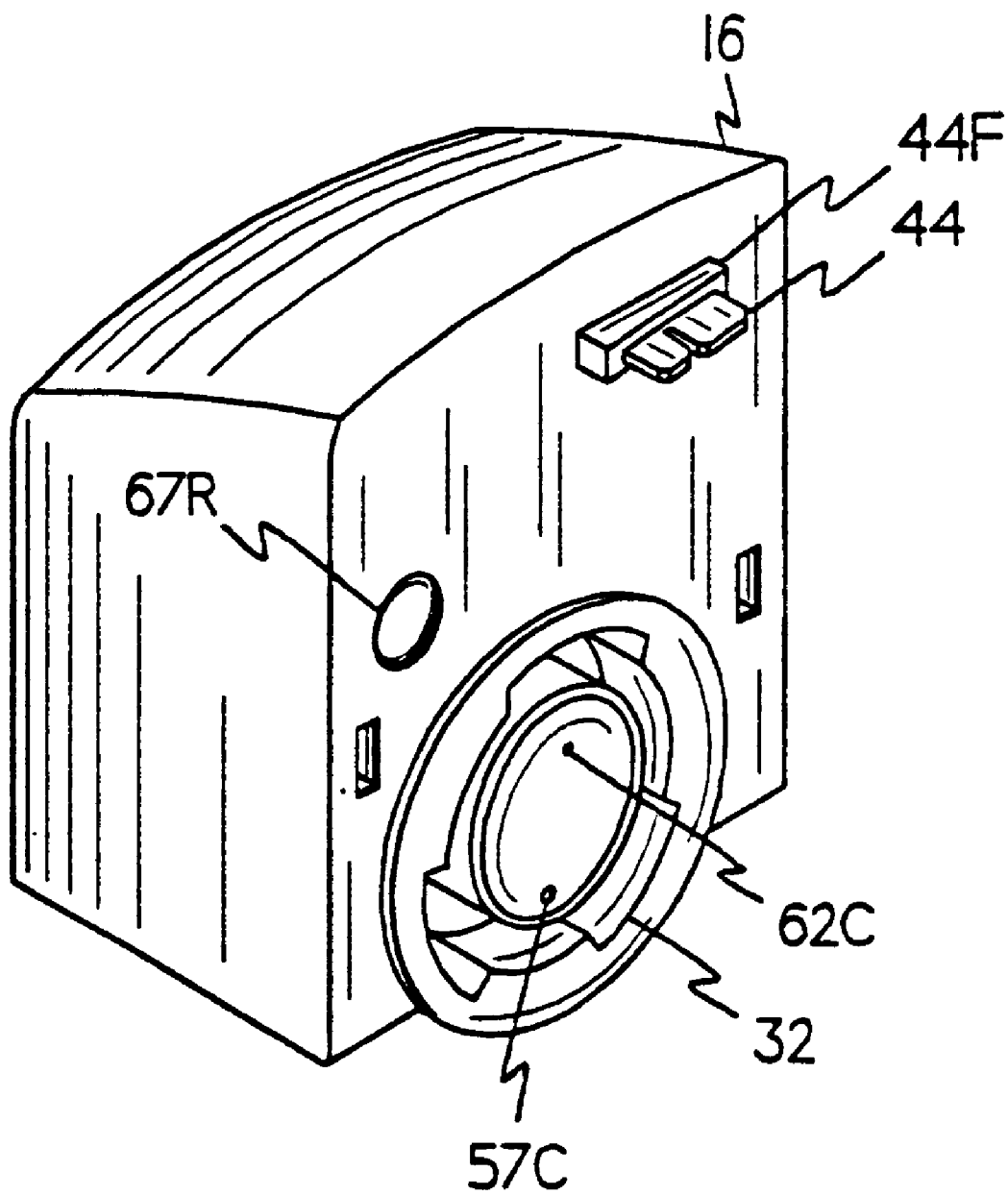
FIG. 7 is a frontal perspective view of the compressor housing of the dental scaler and reservoir system in accordance with the invention shown in FIGS. 1 and 2.
Figure 8:
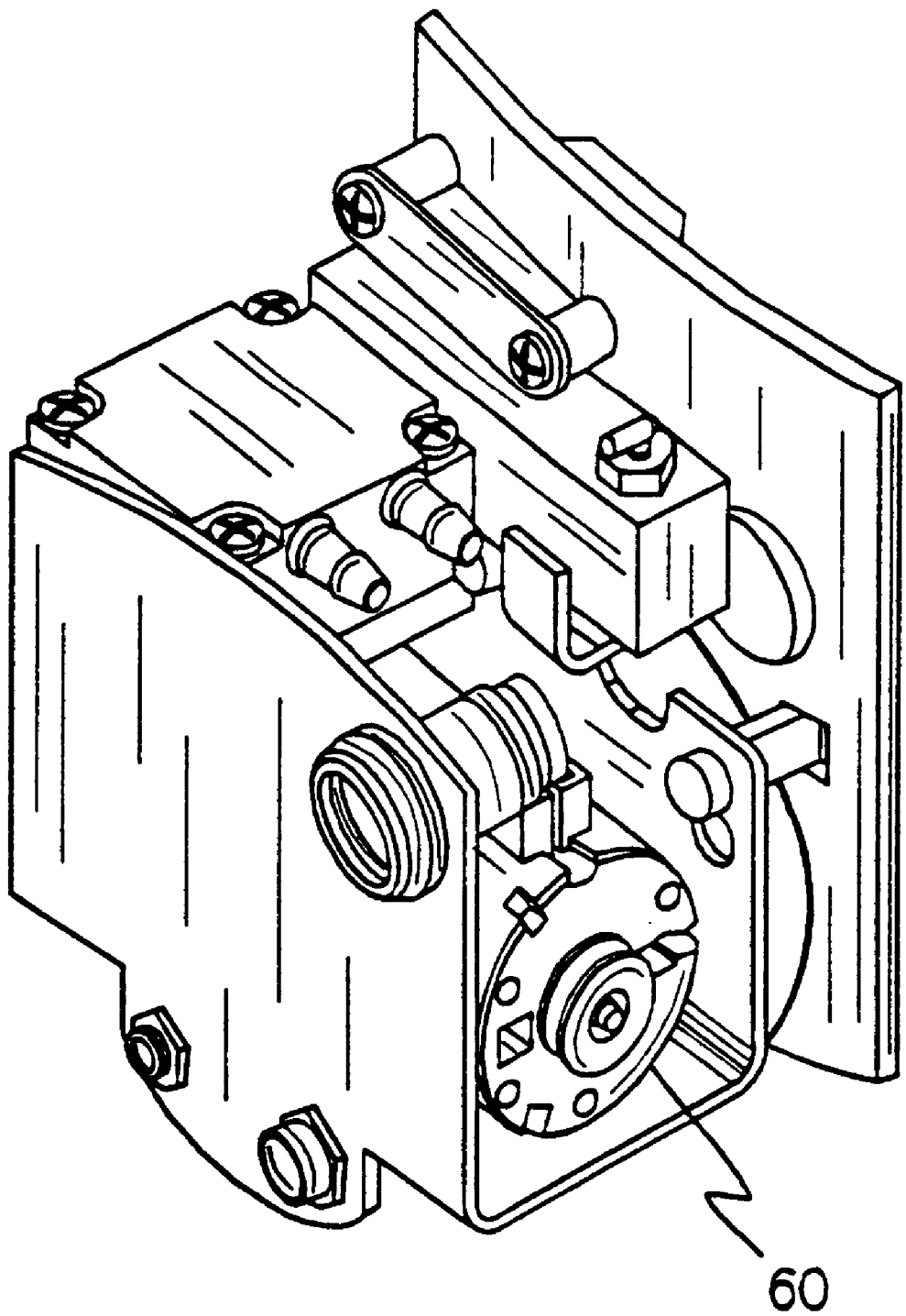
FIG. 8 is a perspective view of the compressor system of the dental scaler and reservoir system in accordance with the invention shown in FIGS. 1 and 2.
Figure 9:
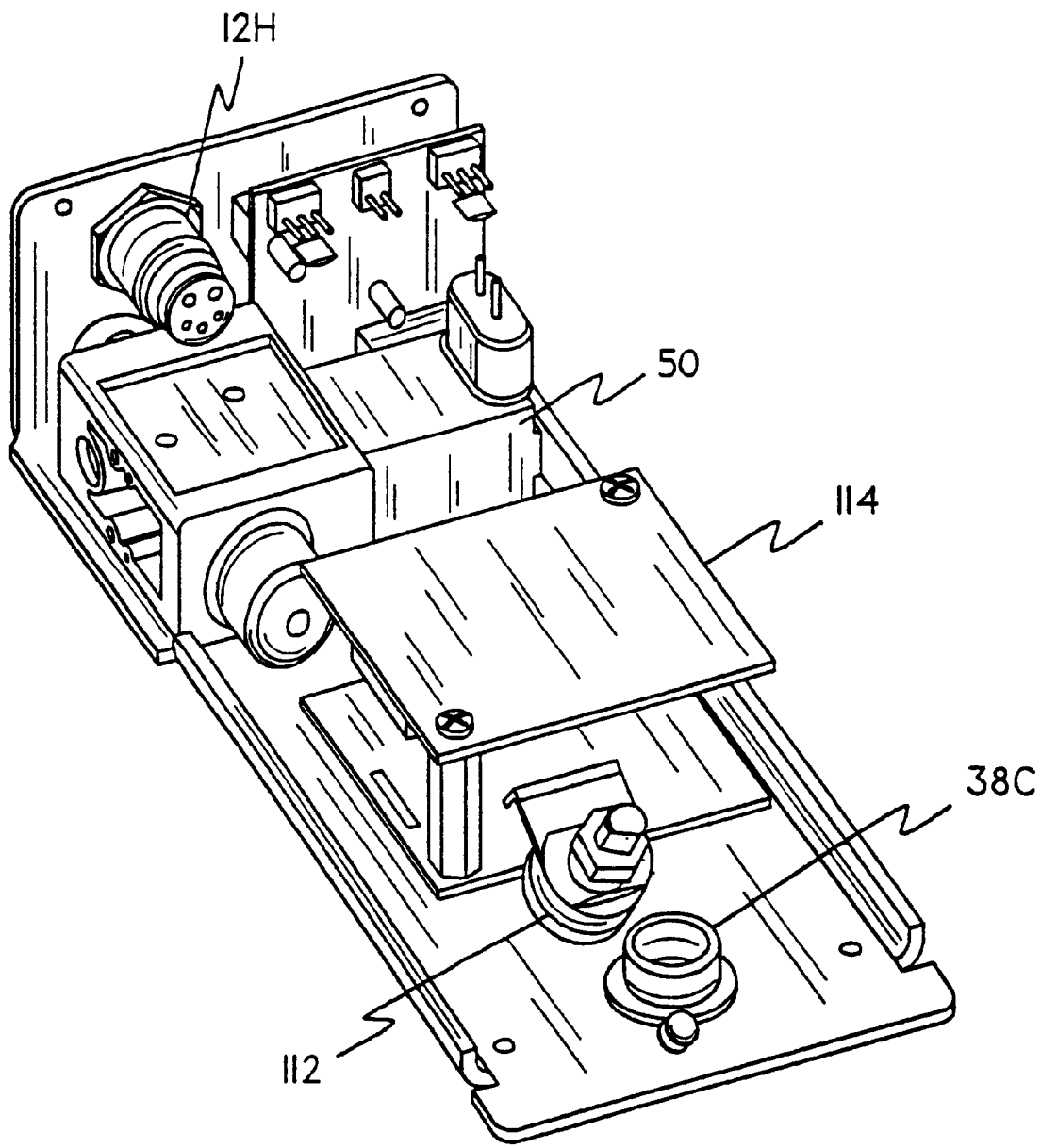
FIG. 9 is a top perspective view of the scaler control system of the dental scaler and reservoir system in accordance with the invention shown in FIGS. 1 and 2.
Figure 10:
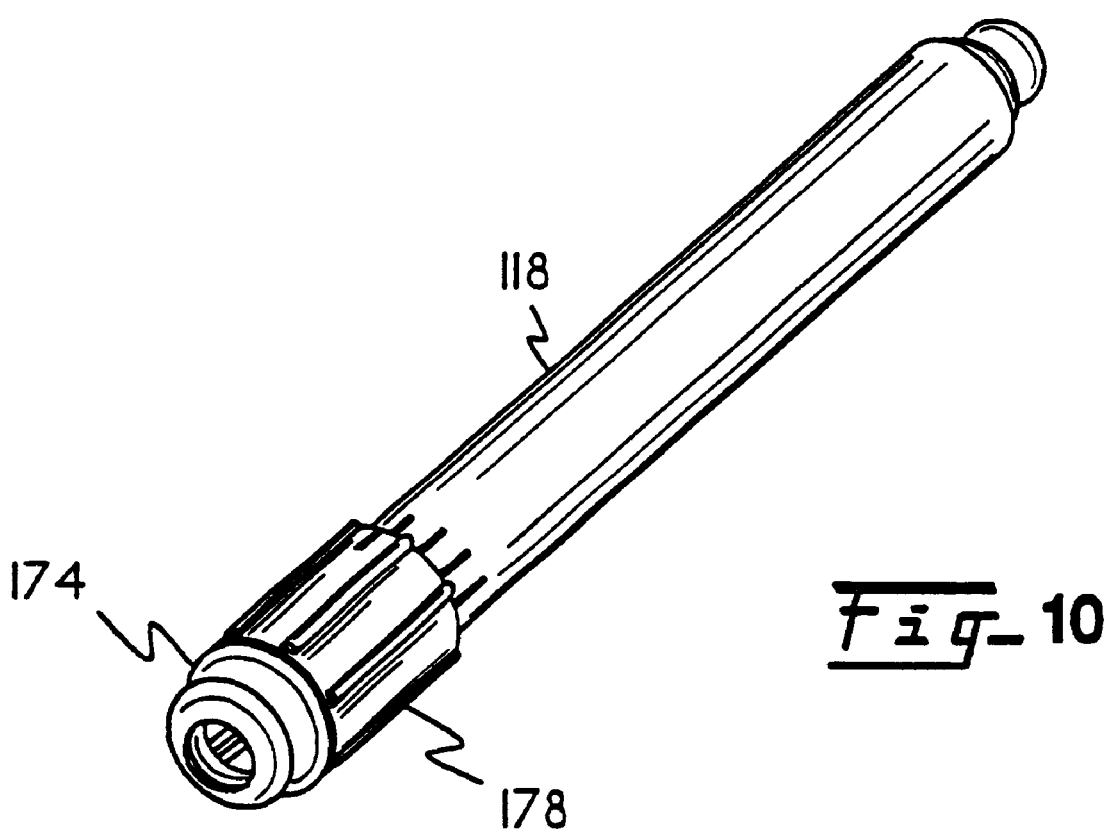
FIG. 10 is a perspective view of a handpiece housing for use with the dental scaler and reservoir system in accordance with the invention shown in FIGS. 1 and 2.
Figure 11:
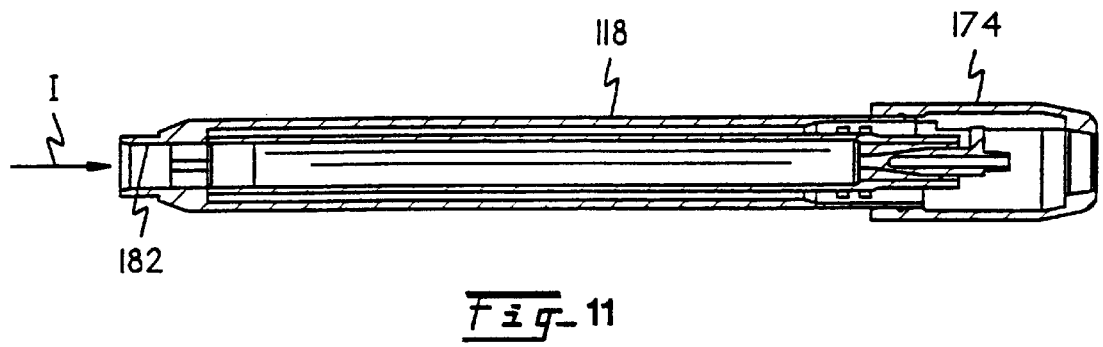
FIG. 11 is a cross-sectional side view of a handpiece housing for use with the dental scaler and reservoir system in accordance with the invention shown in FIGS. 1 and 2.
Figure 12:
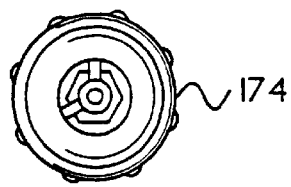
FIG. 12 is an end view of the handpiece housing shown in FIG. 11.
Figure 13:
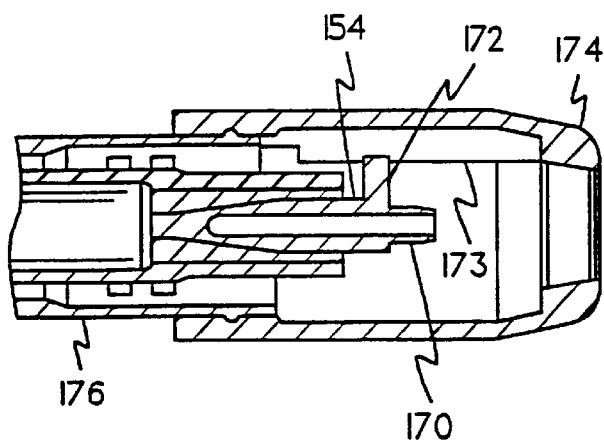
FIG. 13 is a partial cross-sectional side view of the handpiece housing shown in FIG. 11.

The invention provides a method of dental scaling of the invention uses a scaler and reservoir system, comprising: a scaler handpiece having a scaling tip, a scaler housing enclosing a scaler valve, a compressor housing enclosing a reservoir valve and a compressor, a reservoir housing having an inner chamber, the scaler housing is supported by the reservoir housing, and the compressor housing is supported by and connected to the scaler housing and the reservoir housing, the scaler handpiece is connected to the scaler housing, vibrates the tip, and scales a tooth in a patient's tooth by positioning the scaling tip adjacent to the tooth.

The invention provides a dental scaler and reservoir system, comprising: a scaler housing, a scaler valve, a compressor housing, a reservoir valve, a compressor, a reservoir housing having an inner chamber, a handpiece housing having a handpiece valve and a vibrating member. The scaler housing is supported by the reservoir housing. The compressor is connected to compressor conduit. The compressor conduit is connected to the inner chamber of the reservoir housing thereby providing fluid flow communication between the compressor and the inner chamber of the reservoir housing. The inner chamber of the reservoir housing is connected to reservoir conduit. The reservoir conduit is connected to the reservoir valve thereby providing in fluid flow communication between the inner chamber and the reservoir valve. The reservoir valve is connected to handpiece conduit. The handpiece conduit is connected to the handpiece valve thereby providing fluid flow communication between the reservoir valve and the handpiece valve.

The invention provides a method of using a dental scaler system, comprising: providing a first scaler conduit and a dental scaler system comprising a scaler system comprising a scaler housing enclosing a second scaler conduit, and scaler valve, the first scaler conduit not being connected in fluid flow communication with the scaler valve, providing a handpiece system comprising scaler tip and a handpiece housing enclosing a handpiece conduit and handpiece valve, connecting the handpiece conduit in fluid flow communication to the first scaler conduit, conveying a first fluid through the first scaler conduit, scaler valve, and handpiece valve to the scaler tip, connecting the handpiece conduit in fluid flow communication to the second scaler conduit, and conveying a second fluid through the second scaler conduit, and handpiece valve to the scaler tip.

The invention provides a method of using a dental scaler system, comprising providing a dental scaler system comprising a scaler system, a compressor system and a handpiece system. The scaler system comprising a scaler housing enclosing a scaler conduit, and scaler valve. The compressor system comprises a reservoir and a compressor housing enclosing a compressor and a compressor conduit. The reservoir comprising a container enclosing reservoir fluid in a container chamber. The handpiece system comprising scaler tip and a handpiece housing enclosing a handpiece conduit and handpiece valve. The handpiece conduit is connected in fluid flow communication to compressor conduit At least a portion of the reservoir fluid is conveyed through the compressor conduit, scaler valve, and handpiece valve to the scaler tip. The handpiece conduit is connected in fluid flow communication to the scaler conduit and water conveyed through the scaler conduit, and handpiece valve to the scaler tip. When the handpiece conduit is connected in fluid flow communication to the compressor conduit, the compressor housing is connected to the scaler housing and the reservoir housing, and the scaler handpiece is supported by the reservoir housing. When the handpiece conduit is connected in fluid flow communication to the scaler conduit, the scaler housing is supported by a substantially horizontal surface.

The invention provides a method of using a dental scaler system, comprising: providing a scaler system, and a compressor system. The scaler system comprises a scaler housing enclosing an electrical dental scaler circuit connected by an electrical conductor an electrical scaler connector, scaler conduit connected to a scaler valve. The compressor system comprises a reservoir and a compressor housing enclosing an electrical compressor connector connected by an electrical conductor to a compressor and a compressor conduit connected to the reservoir. The reservoir comprises a container enclosing reservoir fluid in a container chamber. The electrical dental scaler circuit produces ultrasonic oscilating current while the electrical compressor connector and the electrical scaler connector are connected, the scaler housing is supported by the reservoir and the compressor conduit is in fluid flow communication with a handpiece. The electrical dental scaler circuit produces ultrasonic osciating current while the electrical compressor connector and the electrical scaler connector are disconnected, the scaler housing and the compressor housing are separated and the scaler conduit is in fluid flow communication with a handpiece.

DETAILED DESCRIPTION OF THE INVENTION

The invention is now described with more particular reference to FIGS. 1 through 16. Dental scaler and reservoir system 10, includes scaler housing 12, which is positioned beside and releasably connected to compressor housing 16 and above reservoir housing 14. Compressor housing 16 is positioned beside and releasably connected to reservoir housing 14. Scaler housing 12 and compressor housing 16 are preferably made of molded rigid polymeric plastic, such as polypropylene. Scaler housing base 12B is preferably made of aluminum. The upper face of scaler housing 12 has handpiece holding groove 11G and power indicator light 11P. Reservoir cap 12C is connected by threads to reservoir fill opening connector 13 of reservoir housing front portion 14R which extends beyond scaler housing 12. Scaler handpiece 18 is connected by flexible conduit 20 to compressor housing 16. Between uses handpiece 18 is supported by groove. Front feet 24 and 26 and rear 24R, and 26R are connected to reservoir housing 14. Power control knob 22 is connected through scaler housing 12 to switch 112 of scaler circuit 114 shown in FIG. 16. When the compressor is in use, compressor housing 16 is connected by handpiece cord connector 16H to handpiece connector 20C, by an electrical foot switch cord connector 16F to a foot switch, and by an electrical power cord connector 16P to an electrical power outlet.

With more particular reference to FIGS. 1 through 9 is seen compressor housing 16 has a one sixth turn connector 32 and reservoir housing 14 has a one sixth turn connector 34. When dental scaler and reservoir system 10 is in assembled position one sixth turn connector 34 engages one sixth turn connector 32. Scaler housing 12 has snap fit catch 38. Snap fit connector 38C connected catch 38 to the scaler housing 12. Reservoir housing 14 is preferably made of molded rigid polymeric plastic, such as polypropylene, and has snap fit connector 40. When dental scaler and reservoir system 10 is in assembled position snap fit connector 40 engages snap fit catch 38. When dental scaler and reservoir system 10 is in assembled position inner compressor control connector 44 engages and provides electrical connection to outer compressor control connector 46. When dental scaler and reservoir system 10 is in assembled position compressor control connector flange 44F extends into compressor control connector recess wall 44R. Front feet 24S and 26S and rear 24RS and 26RS are connected to scaler housing base 12B.

When dental scaler and reservoir system 10 is in assembled position conduit connector 67 fits into recess 67R. When the scaler is being used without the compressor scaler housing 12 is connected by handpiece cord connector 12H to handpiece connector 20C, by an electrical foot switch cord connector 12F to a foot switch, and by an electrical power cord connector 12P to a power outlet.

With more particular reference to FIGS. 10 through 13 is seen polisher handpiece 118 having valve 154 and conduit connector 170. Connector 170 has arm 172 and is enclosed by rotatable handpiece cap 174. Handpiece cap 174 is rotatably connected to handpiece body 176. Handpiece cap 174 has ribs 178. Connector 170 is adjusted by rotating handpiece cap 174. Arm 172 fits into a groove 173 in cap 174 and turns connector 170 as handpiece cap 174 is rotated. Connector 170 is connected to tube 170T. Ultrasonic scaling insert 180 is positioned into the insert chamber enclosed by insert channel wall 182 and within coil 18C. Coil 18C is connected by electrical conductor 18E to pin 18P. Electrical conductor is connected to pin 18P. Connector 170 and electrical conductor 18E extend through conduit 20 to handpiece connector 20C. 18E Ultrasonic scaling tip 184 is connected to insert 180.

Figure 14:
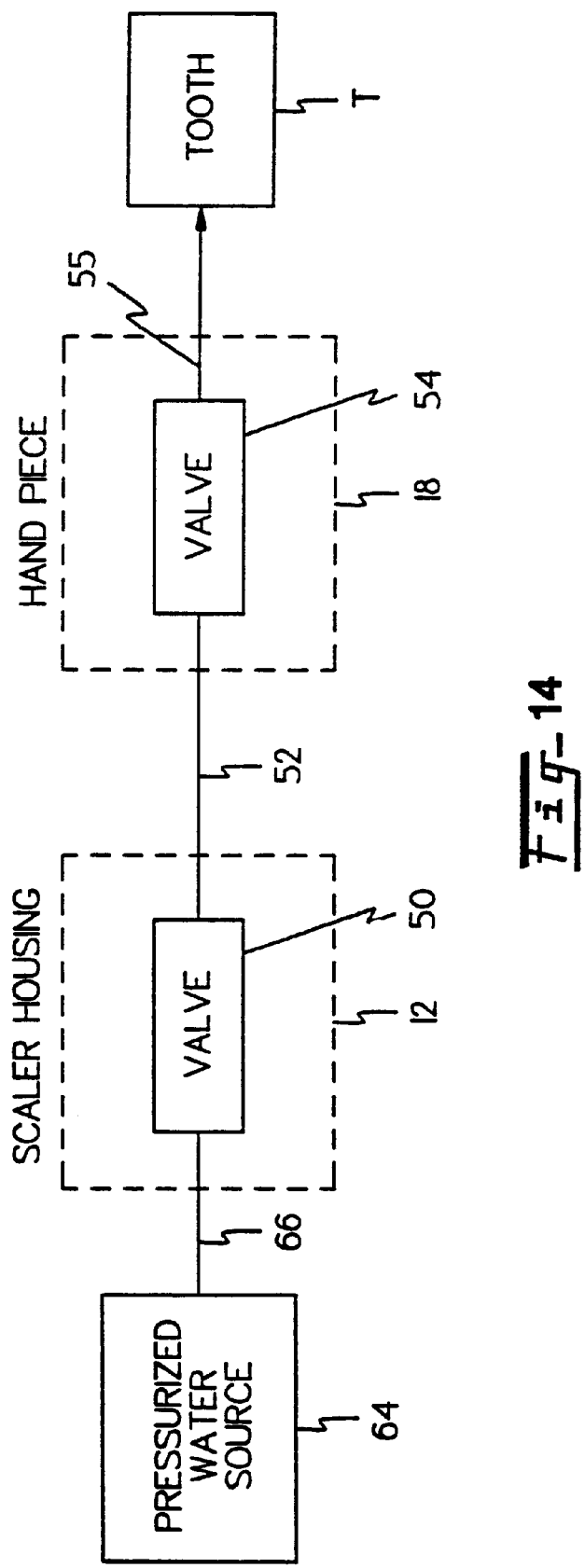
FIG. 14 is a schematic diagram of the use of the dental scaler system in accordance with the invention shown in FIGS. 4 through 6.

With more particular reference to FIG. 14 is seen an operational dental scaler system using dental scaler 11. Conduit 66 is connected through conduit connector 67 to source of pressurized fluid 64. The pressurized fluid is for example liquid water at 23° C. and from about 15 to about 60 psig. Dental scaler 11 is operated to convey fluid from source of pressurized fluid 64 through conduit 66, valve 50, conduit 52, valve 54 conduit 55 to tooth T. In use the flow of fluid through conduit 55 is adjustable from about 5 ml per minute to about 55 ml per minute. In use tip 184 is vibrated at a frequency of about 23,500 to about 26,500 Hz.

Handpiece 18 is connected to dental scaler 11 through flexible conduit 20. Dental scaler 11 is then operated to convey fluid from source of pressurized fluid 64 through conduit 66, valve 50, conduit 52, valve 154 to tooth T.

Figure 15:
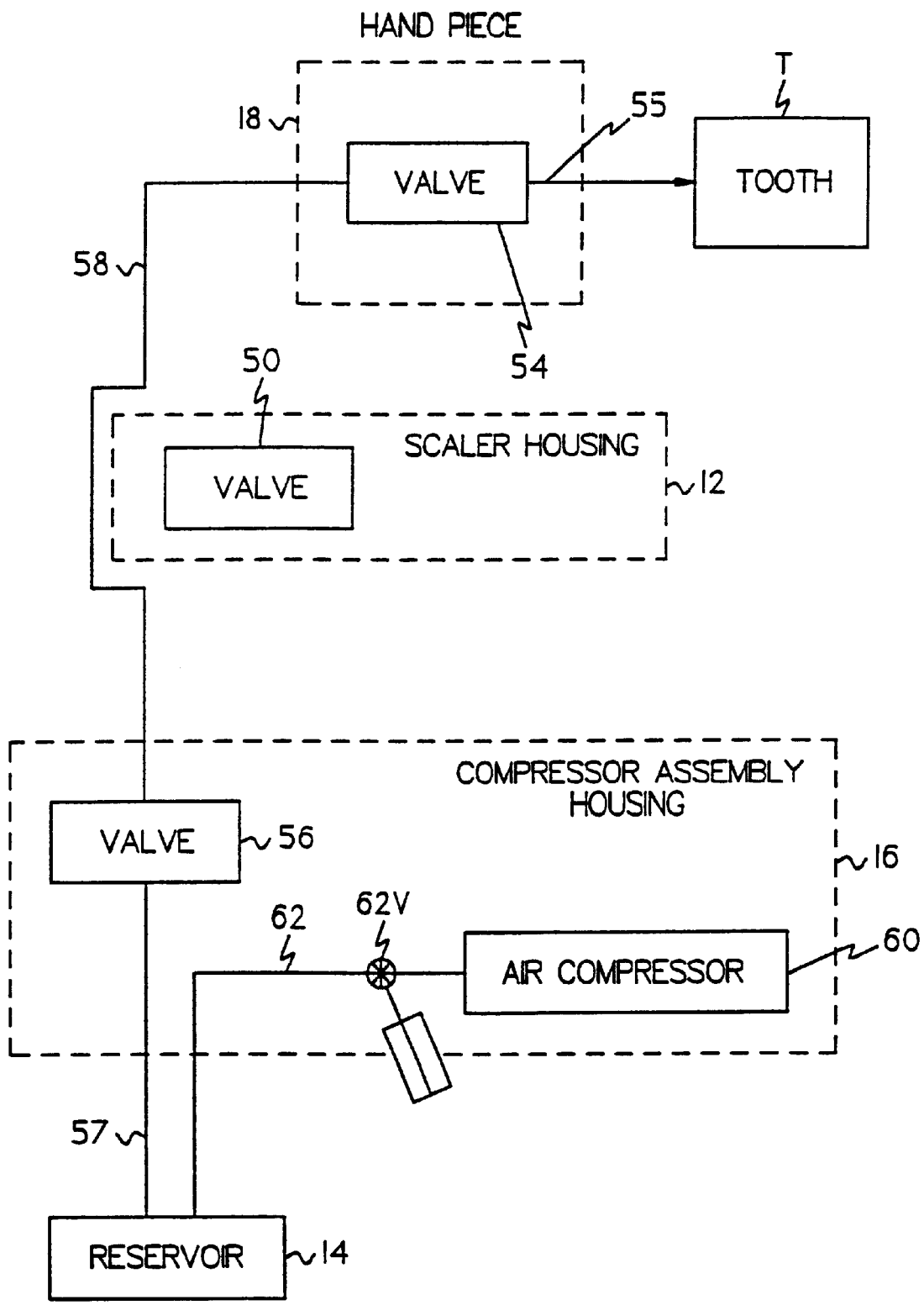
FIG. 15 is a schematic diagram of the dental scaler and reservoir system in accordance with the invention shown in FIGS. 1 and 2.

Dental scaler and reservoir system 10 is operated to convey fluid as shown in FIG. 15. Dental scaler and reservoir system 10 is operated to convey fluid from a chamber enclosed by reservoir 14 through connector opening 57C, conduit 57, valve 56, conduit 58, valve 54 conduit 55 to tooth T. Compressed air from compressor 60 is coveyed through conduit 62 and connector opening 62C into the space above the fluid in reservoir 14 to raise the pressure above the fluid preferably to from about 15 to about 20 psig. When valve 56, and valve 54 are open compressed air in the space above the fluid in reservoir 14 forces the fluid from reservoir 14 through conduit 57, valve 56, conduit 58, valve 54 conduit 55 to tooth T. Optionally, conduit 62 is vented to the atmosphere through push button pressure relief valve 62V. In use the flow of fluid through conduit 55 is adjustable from about 5 ml per minute to about 55 ml per minute. In use tip 184 is vibrated at a frequency of about 23,500 to about 26,500 Hz. Preferably valves 50 and 56 are a solenoid valves.

Figure 16:
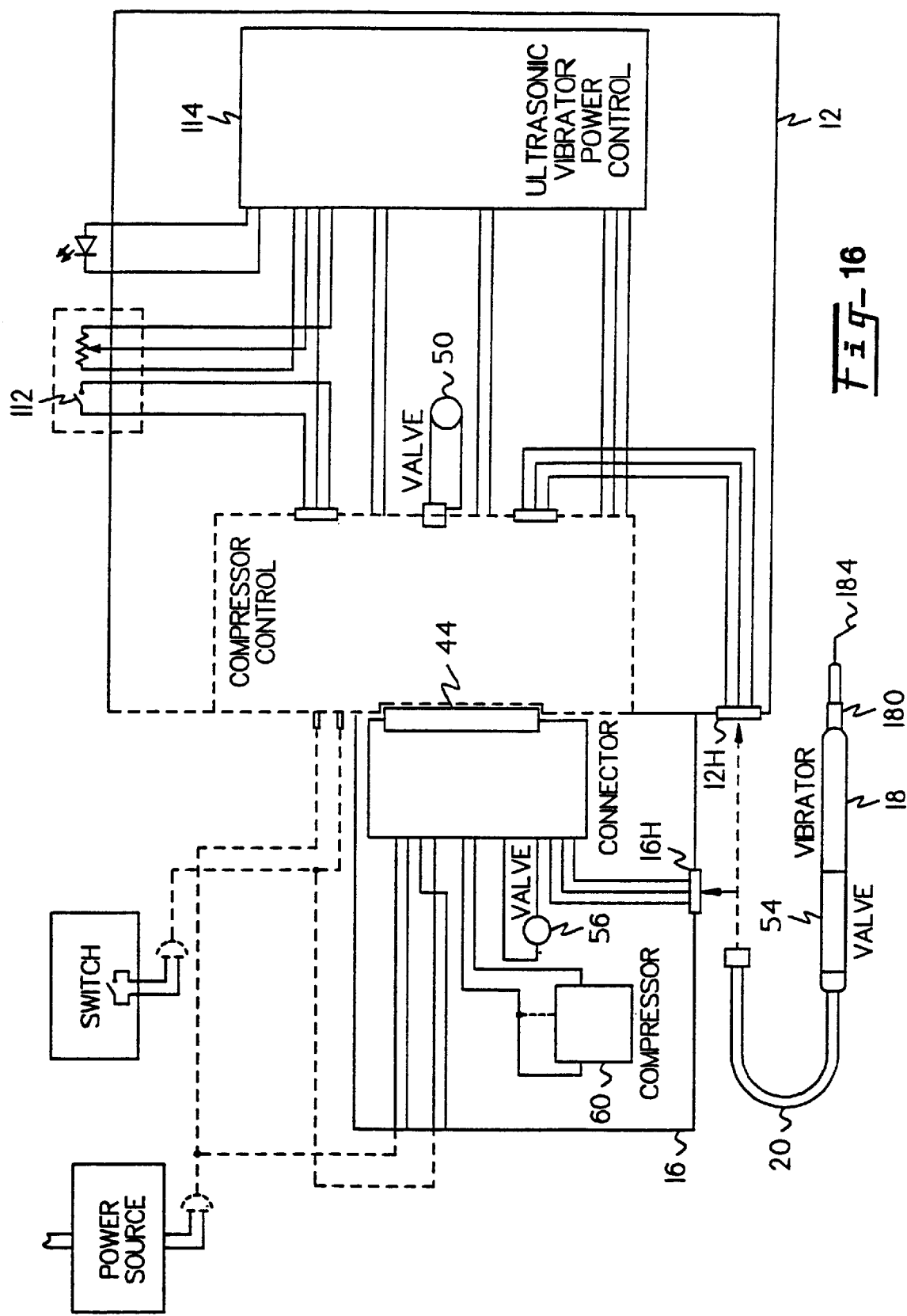
FIG. 16 is a schematic diagram circuitry for the dental scaler and reservoir system in accordance with the invention shown in FIGS. 1 and 2.

With more particular reference to FIG. 16 is seen circuitry 114 for the dental scaler system 11. Circuitry 114 is for example a system for continuous control of tip vibration disclosed by Jovanovic et al in U.S. Pat. No. 5,754,016 incorporated herein by reference in its entirety. In use circuitry 114 generates a current oscillating at an ultrasonic frequency and this current is conducted by electrical conductors to coil enclosed within handpiece housing 18.

Thus, dental scaler and reservoir system 10 comprises a scaler housing 12, a scaler valve, a compressor housing 16, a reservoir valve, a compressor, a reservoir housing 14 having an inner chamber, a handpiece housing 18 having a handpiece valve and a vibrational member. The scaler housing 12 is supported by the reservoir housing 14. The compressor is connected to compressor conduit. The compressor conduit is connected to the inner chamber of the reservoir housing thereby providing fluid flow communication between the compressor and the inner chamber of the reservoir housing. The inner chamber of the reservoir housing is connected to reservoir conduit. The reservoir conduit is connected to the reservoir valve thereby providing in fluid flow communication between the inner chamber and the reservoir valve. The reservoir valve is connected to handpiece conduit. The handpiece conduit is connected to the handpiece valve thereby providing fluid flow communication between the reservoir valve and the handpiece valve.

The reservoir container 14 is shaped to be easily wiped clean. All cords and tubing are easily removed from the unit. Preferably, an external switching power supply is utilized to give an output of 30 volts of direct current (DC) with an input voltage of 90–264 volts alternating current (VAC), 47–63 Hz. Preferably, a disposable inline filter is provided on the lavage inlet hose. A lavage flow control valve is provided in the handpiece. The handpiece rest groove 11G is integral to the top housing to ensure ease of cleaning. Preferably, the on/off control is combined with the rotary power control for ease of use. Power indicator light 11P is preferably a green LED and located below the power control to indicate DC power on. Preferably, all unit heat-generating components are isolated from the lavage path to reduce handpiece heat generation. The lavage minimum input pressure is preferably 15 psig. This allows adequate lavage flow through the unit in areas with low water pressure.

Compressor housing 16 and reservoir 14 are adapted for use with scaler housing 12, all lines are removed from scaler housing 12. Reservoir 14 and scaler housing 12 are snapped together. The foot control, and handpiece connections are made in the back of compressor housing 16. All electrical connections are made via inner compressor control connector 44 (for example an interconnect board connector) and outer compressor control connector 46 (for example a mating receptacle) supported by scaler housing 12. The lavage passes through valve 50, which preferably is an integral solenoid and pressure regulator. The output pressure is preferably set to 15±1 psig. This is to maintain consistent lavage output with varying input pressure. The solenoid is downstream of the regulator. Flow run on is minimized when the footswitch is depressed and released. An integral phase lock loop system is preferably used to ensure peak performance for a multitude of different 25 kHz scaling inserts. A voltage sensing circuit is preferably used to reduce the effects load and line variations that may be seen at the output of the switching power supply.

When compressor housing 16 and reservoir 14 are used with scaler 12, the footswitch, power supply, water inlet hose and handpiece hose are removed from the unit. The scaler 12 is preferably connected to compressor housing 16 and reservoir 14. They are connected, for example, by plugging compressor control connector 44 (for example a rear PCB edge card connector) from compressor housing 16 into the (PCD edge) card receptacle 46 of scaler housing 12. Scaler housing 12 is snapped together with the compressor housing 16 and reservoir 14. Perferably the retaining mechanism is a plastic latch and strike. The catch 38 is connected to the scaler base 12B by catch connector 38C. The footswitch, power supply and handpiece are connected to their respective locations on the rear of compressor housing 16. Power, footswitch and handpiece connections are preferably made via the PCB edge card connection.

A small diaphragm air compressor is preferably utilized to pressurize the reservoir chamber in reservoir container 14 to 15–19 psig. This provides pressure to propel the lavage liquid from reservoir 14. A lavage outlet 57C is located on the bottom of one end of one sixth turn connector 32 adjacent to and enclosed by an opening wall on the end of reservoir container 14 opposite from cap 12C. This preferably is connected to an isolation solenoid valve. The output of this solenoid valve is then preferably connected to the handpiece receptacle lavage port. This gives the benefit of the fluid path only passing through the reservoir container 14. Utilizing all autoclavble components preferably enables the entire unit is autoclaved.

Preferably, the reservoir container 14 holds a volume of 450–500 ml of liquid such as sterile water. The reservoir container 14 is mated to the rear dispenser with a 60° turn. The front feet are integral to the reservoir container 14. An O-ring between the container 14 and the rear support create the seal. Preferably, the reservoir container 14 is steam autoclavable.

In accordance with a preferred embodiment of the invention is provided a dental scaler system, comprising: a scaler comprising a scaler housing enclosing a scaler conduit and scaler valve and a handpiece comprising a handpiece housing enclosing a handpiece valve and a handpiece conduit, the handpiece valve is connected in fluid flow communication through the scaler conduit and the handpiece conduit to the scaler valve. Preferably, the handpiece further comprises a scaling tip, and the handpiece valve is connected in fluid flow communication to the scaling tip.

In accordance with a preferred embodiment of the invention is provided a method of using a dental scaler system, comprising: providing a second scaler conduit and a dental scaler system comprising a scaler system comprising a scaler housing enclosing a first scaler conduit, and scaler valve. The second scaler conduit not is connected in fluid flow communication with the scaler valve. A handpiece system is provided comprising scaler tip and a handpiece housing enclosing a handpiece conduit and handpiece valve. The handpiece conduit is connected in fluid flow communication to the scaler conduit. A first fluid is conveyed through the first scaler conduit, scaler valve, and handpiece valve to the scaler tip. A second fluid is conveyed through the second scaler conduit, and handpiece valve to the scaler tip, and the tip is positioned adjacent to a tooth in a patient's mouth to scale the tooth. Preferably, the method further comprises providing a compressor comprising a compressor housing enclosing a reservoir valve and an air compressor, and a reservoir comprising a reservoir housing having a reservoir inner chamber, the reservoir valve is connected in fluid flow communication to the scaler conduit and to the reservoir inner chamber.

In accordance with a preferred embodiment of the invention is provided a method of using a dental scaler system, comprising: providing a dental scaler connected to a tip and a reservoir containing a first liquid, ultrasonically moving the tip while conveying at least a portion of the first liquid to the tip, and ultrasonically moving the tip while conveying at least a portion of a second liquid to the tip. Preferably, first liquid is pressurized in the reservoir by pressurized air conveyed to the reservoir from a compressor enclosed in a compressor housing and the compressor housing is connected to the compressor housing. Preferably, the second liquid is water conveyed to the dental scaler system by a water distribution conduit system connecting a plurality of locations.

In accordance with a preferred embodiment of the invention is provided a method of using a dental scaler system, comprising: providing a first scaler conduit and a dental scaler system comprising a scaler system comprising a scaler housing enclosing a second scaler conduit, and scaler valve. The first scaler conduit is not connected in fluid flow communication with the scaler valve. A handpiece system is provided comprising scaler tip and a handpiece housing enclosing a handpiece conduit and handpiece valve, connecting the handpiece conduit in fluid flow communication to the first scaler conduit. A first fluid is conveyed through the first scaler conduit, scaler valve, and handpiece valve to the scaler tip. The handpiece conduit is connected in fluid flow communication to the second scaler conduit, and a second fluid is conveyed through the second scaler conduit, and handpiece valve to the scaler tip. Preferably, the dental scaler system further comprising positioning the tip adjacent to a tooth in a patient's mouth and scaling the tooth. Preferably, the method of using a dental scaler system further comprising providing a compressor system comprising a compressor housing enclosing a reservoir valve and an air compressor, and a reservoir system comprising a reservoir housing having a reservoir inner chamber, the reservoir valve being connected in fluid flow communication to the second scaler conduit and to the reservoir inner chamber. Preferably, the reservoir housing is releasably connected to the scaler housing through a releasable connectors, whereby lifting the scaler housing lifts and supports the the reservoir housing through the releasable connectors. Preferably, the reservoir housing is releasably connected to the compressor housing through a rotatable connector, whereby lifting the compressor housing lifts and supports the the reservoir housing through the rotatable connector. Preferably, the reservoir housing has at least two reservoir housing feet and the scaler housing has at least two scaler housing feet, and the reservoir housing feet are supported by a substantially horizontal surface and the scaler housing feet are supported by the reservoir housing.

In accordance with a preferred embodiment of the invention is provided a method of using a dental scaler system, comprising: providing a dental scaler system comprising a scaler system, a compressor system and a handpiece system. The scaler system comprising a scaler housing enclosing a scaler conduit, and scaler valve. The compressor system comprising a reservoir and a compressor housing enclosing a compressor and a compressor conduit the reservoir comprising a container enclosing reservoir fluid in a container chamber. The handpiece system comprising scaler tip and a handpiece housing enclosing a handpiece conduit and handpiece valve. The handpiece conduit is connected in fluid flow communication to compressor conduit. At least a portion of the reservoir fluid is conveyed through the compressor conduit, scaler valve, and handpiece valve to the scaler tip. The handpiece conduit is connected in fluid flow communication to the scaler conduit and water conveyed through the scaler conduit, and handpiece valve to the scaler tip. Preferably, the method of using a dental scaler system further comprises positioning the tip adjacent to a tooth in a patient's mouth and scaling the tooth. Preferably, when the handpiece conduit is connected in fluid flow communication to the compressor conduit, the compressor housing is connected to the scaler housing and the reservoir housing, and the scaler handpiece is supported by the reservoir housing. Preferably, when the handpiece conduit is connected in fluid flow communication to the scaler conduit, the scaler housing is supported by a substantially horizonal surface.

In accordance with a preferred embodiment of the invention is provided a method of using a dental scaler system, comprising: providing a scaler system, and a compressor system. The scaler system comprises a scaler housing enclosing an electrical dental scaler circuit connected by an electrical conductor an electrical scaler connector, scaler conduit connected to a scaler valve. The compressor system comprises a reservoir and a compressor housing enclosing an electrical compressor connector connected by an electrical conductor to a compressor and a compressor conduit connected to the reservoir. The reservoir comprises a container enclosing reservoir fluid in a container chamber. The electrical dental scaler circuit produces ultrasonic oscilating current while the electrical compressor connector and the electrical scaler connector are connected, the scaler housing is supported by the reservoir and the compressor conduit is in fluid flow communication with a handpiece. The electrical dental scaler circuit produces ultrasonic oscilating current while the electrical compressor connector and the electrical scaler connector are disconnected, the scaler housing and the compressor housing are separated and the scaler conduit is in fluid flow communication with a handpiece. Preferably, the scaler housing encloses a the scaler conduit. Preferably, the method further comprises providing a handpiece system comprises a scaler tip and a handpiece housing enclosing a handpiece conduit and handpiece valve, connecting the handpiece conduit in fluid flow communication to the scaler conduit, conveying water through the scaler conduit, and handpiece valve to the scaler tip, connecting the handpiece conduit in fluid flow communication to compressor conduit, and conveying at least a portion of the reservoir fluid through the compressor conduit, scaler valve, and handpiece valve to the scaler tip.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A dental scaler and reservoir system, comprising:
   a scaler housing,
   a compressor housing enclosing a reservoir valve and a compressor,
   a reservoir housing having an inner chamber, and
   a handpiece housing enclosing a handpiece valve, a handpiece conduit, and a vibrational member,
      said scaler housing being positioned above and supported by said reservoir housing, and
      said compressor housing being positioned beside, supported by and connected to said scaler housing and said reservoir housing, said compressor is connected to a compressor conduit, said compressor conduit being connected to said inner chamber of said reservoir housing thereby providing fluid flow communication between said compressor and said inner chamber of said reservoir housing,
      said inner chamber of said reservoir housing being connected to a reservoir conduit, said reservoir conduit being connected to said reservoir valve thereby providing in fluid flow communication between said inner chamber and said reservoir valve,
      said reservoir valve being connected to a handpiece conduit, said handpiece conduit being connected to said handpiece valve thereby providing fluid flow communication between said reservoir valve and said handpiece valve.

2. A dental scaler and reservoir system, comprising:
   a scaler housing, a scaler valve,
   a compressor housing, a reservoir valve, a compressor,
   a reservoir housing having an inner chamber,
   a handpiece housing having a handpiece valve and a vibrational member, said scaler housing being positioned above and supported by said reservoir housing, and said compressor housing being positioned beside, supported by and connected to said scaler housing and said reservoir housing, said compressor being connected to a compressor conduit said compressor conduit being connected to said inner chamber of said reservoir housing thereby providing fluid flow communication between said compressor and said inner chamber of said reservoir housing, said Inner chamber of said reservoir housing being connected to a reservoir conduit, said reservoir conduit being connected to said reservoir valve thereby providing in fluid flow communication between said inner chamber and said reservoir valve, said reservoir valve being connected to a handpiece conduit, said handpiece conduit being connected to said handpiece valve thereby providing fluid flow communication between said reservoir valve and said handpiece valve.

3. A method of dental scaling comprising:

providing a scaler handpiece having a scaling tip, a scaler housing enclosing a scaler valve, a compressor housing enclosing a reservoir valve and a compressor, a reservoir housing having an inner chamber, said scaler housing being positioned above and supported by said reservoir housing, and said compressor housing being positioned beside, supported by and connected to said scaler housing and said reservoir housing, said scaler handpiece being connected to said scaler housing, said compressor housing being releasably connected to said scaler housing and said reservoir housing, said compressor being connected in fluid flow communication by a compressor conduit to said inner chamber of said reservoir housing, said inner chamber of said reservoir housing being connected in fluid flow communication to said reservoir valve, said reservoir valve being connected in fluid flow communication to a handpiece conduit, said handpiece conduit being connected in fluid flow communication to said handpiece valve, ultrasonically vibrating said tip, and scaling a tooth in a patient's mouth by positioning said scaling tip adjacent to said tooth.

4. A dental scaler and reservoir system, comprising:

scaler handpiece having a handpiece valve, a scaler comprising a scaler housing enclosing a scaler conduit, a compressor comprising a compressor housing enclosing a reservoir valve and an air compressor, and a reservoir comprising a reservoir housing having a reservoir inner chamber, said compressor housing being releasably connected to said scaler housing and said reservoir housing, said compressor being connected in fluid flow communication by a compressor conduit to said inner chamber of said reservoir housing, said inner chamber of said reservoir housing being connected in fluid flow communication to said reservoir valve, said reservoir valve being connected in fluid flow communication to a handpiece conduit, said handpiece conduit being connected in fluid flow communication to said hand piece valve, said scaler housing being positioned above and supported by said reservoir housing, and compressor housing being positioned beside, supported by and connected to said scaler housing and said reservoir housing, said reservoir valve being connected in fluid flow communication to said scaler conduit and to said reservoir inner chamber.

5. The dental scaler and reservoir system of claim 4 wherein said scaler housing is supported by said reservoir housing and said compressor housing.

6. The dental scaler and reservoir system of claim 4 wherein said scaler handpiece further comprises a handpiece housing enclosing said handpiece valve and said handpiece conduit.

7. A method of using a dental scaler system, comprising:

providing a dental scaler system comprising a first scaler conduit and a scaler comprising a scaler housing enclosing a second scaler conduit, and scaler valve, said first scaler conduit not being connected in fluid flow communication with said scaler valve, providing a handpiece system comprising scaler tip and a handpiece housing enclosing a handpiece conduit and handpiece valve, connecting said handpiece conduit in fluid flow communication to said second scaler conduit, conveying a first fluid through said second scaler conduit, scaler valve, and handpiece valve to said scaler tip, connecting said handpiece conduit in fluid flow communication to said first scaler conduit, and conveying a second fluid through said first scaler conduit, and handpiece valve to said scaler tip.

8. The method of using a dental scaler system of claim 7 further comprising positioning said tip adjacent to a tooth in a patient's mouth and scaling said tooth.

9. The method of using a dental scaler system of claim 7 further comprising providing a compressor and a reservoir, said compressor comprising a compressor housing enclosing a reservoir valve and an air compressor, and said reservoir comprising a reservoir housing enclosing a reservoir inner chamber, said reservoir valve being connected in fluid flow communication to said first scaler conduit and to said reservoir inner chamber.

10. The method of using a dental scaler system of claim 9 wherein said reservoir housing is releasably connected to said scaler housing through releasable connectors, whereby lifting said scaler housing lifts and supports said said reservoir housing through said releasable connectors.

11. The method of using a dental scaler system of claim 9 wherein said reservoir housing is releasably connected to said compressor housing through a rotatable connector, whereby lifting said compressor housing lifts and supports said said reservoir housing through said rotatable connector.

12. The method of using a dental scaler system of claim 9 wherein said reservoir housing has at least two reservoir housing feet and said scaler housing has at least two scaler housing feet, and said reservoir housing feet are supported by a substantially horizontal surface and said scaler housing feet are supported by said reservoir housing.

13. A method of using a dental scaler system, comprising:

providing a dental scaler connected to a tip and a reservoir containing a first liquid, said dental scaler being positioned above and supported by said reservoir, ultrasonically moving said tip while conveying at least a portion of said first liquid to said tip, and ultrasonically moving said tip while conveying at least a portion of a second liquid to said tip.

14. The method of claim 13 wherein said first liquid is pressurized in said reservoir by pressurized air conveyed to said reservoir from a compressor enclosed in a compressor housing and said compressor housing is connected to and positioned beside said reservoir.

15. The method of claim 13 wherein said second liquid is water conveyed to said dental scaler system by a water distribution conduit system.

16. A method of using a dental scaler system, comprising: providing a dental scaler system comprising a scaler, a compressor system and a handpiece, said scaler comprising a scaler housing enclosing a scaler conduit, connected to a scaler valve, said compressor system comprising a reservoir and a compressor housing enclosing a compressor connected to a compressor conduit, said reservoir comprising a container enclosing reservoir fluid in a container chamber, said handpiece comprising scaler tip and a handpiece housing enclosing a handpiece conduit connected to a handpiece valve, said dental scaler being positioned above and supported by said reservoir, said reservoir fluid being in fluid flow communication from said reservoir through said compressor conduit, said scaler valve, and said handpiece valve to said scaler tip, connecting said handpiece conduit in fluid flow communication to said compressor conduit, conveying at least a portion of said reservoir fluid through said compressor conduit, scaler valve, and handpiece valve to said scaler tip, connecting said handpiece conduit in fluid flow communication to said scaler conduit, and conveying water through said scaler conduit, and handpiece valve to said scaler tip.

17. The method of using a dental scaler system of claim 16 further comprising positioning said tip adjacent to a tooth in a patient's mouth and scaling said tooth.

18. The method of using a dental scaler system of claim 16 wherein when said handpiece conduit is connected in fluid flow communication to said compressor conduit, said compressor housing is connected to said scaler housing and said reservoir housing, and said scaler handpiece is supported by said reservoir housing.

19. The method of using a dental scaler system of claim 16 wherein when said handpiece conduit is connected in fluid flow communication to said scaler conduit, said scaler housing is supported by a substantially horizonal surface.

20. The method of using a dental scaler system of claim 16 wherein said scaler housing is positioned above and supported by said container.

21. A method of connecting a dental scaler, comprising:

providing a dental scaler, and a compressor, said dental scaler comprising a scaler housing enclosing an electrical dental scaler circuit connected by an electrical conductor to an electrical scaler connector, and a scaler conduit connected to a scaler valve, said compressor comprising a reservoir and a compressor housing enclosing an electrical compressor connector connected by an electrical conductor to a compressor and a compressor conduit connected to said reservoir, said reservoir comprising a container enclosing reservoir fluid in a container chamber, said dental scaler being positioned above and supported by said reservoir, and connecting said electrical compressor connector to said electrical scaler connector.

22. A method of dental scaling comprising:

providing a scaler and reservoir system, comprising: a scaler handpiece having a scaling tip, a scaler housing, a compressor housing enclosing a reservoir valve and a compressor, a reservoir housing having an inner chamber, said scaler housing being supported by said reservoir housing, and said compressor housing being supported by and connected to said scaler housing and said reservoir housing, said scaler handpiece being connected to said scaler housing, said compressor being connected to provide fluid flow communication between said compressor and said inner chamber of said reservoir housing, said inner chamber of said reservoir housing being connected to provide fluid flow communication between said inner chamber and said reservoir valve, said reservoir valve being connected to provide fluid flow communication between said reservoir valve and said handpiece valve, vibrating said tip, and scaling a tooth in a patient's mouth by positioning said scaling tip adjacent to said tooth.

23. A method of dental scaling comprising:

providing a scaler and reservoir system, comprising: a scaler handpiece having a scaling tip, a compressor housing enclosing a reservoir valve and a compressor, a scaler housing positioned above and supported by a reservoir housing having an inner chamber, said compressor housing being supported beside and connected to said scaler housing, said compressor housing being supported beside and connected to said reservoir housing, said scaler handpiece being connected to said scaler housing, said compressor being connected to provide fluid flow communication between said compressor and said inner chamber of said reservoir housing, said inner chamber of said reservoir housing being connected to provide fluid flow communication between said inner chamber and said reservoir valve, said reservoir valve being connected to provide fluid flow communication between said reservoir valve and said handpiece valve.

vibrating said tip, and scaling a tooth in a patients mouth by positioning said scaling tip adjacent to said tooth.

24. A method of using a dental scaler system comprising:

providing a dental scaler connected to a tip and a reservoir containing a first liquid, said dental scaler being positioned above and supported by said reservoir, ultrasonically moving said tip while conveying at least a portion of said first liquid to said tip.

* * * * *